United States Patent [19]

Miyake et al.

[11] Patent Number: 5,584,877
[45] Date of Patent: Dec. 17, 1996

[54] ANTIBACTERIAL VASCULAR PROSTHESIS AND SURGICAL SUTURE

[75] Inventors: Shinichi Miyake; Shigehiko Ito; Yumiko Oka, all of Osaka; Jun-ichi Kambayashi, Hyogo-ken; Kazuhiro Okahara, Osaka, all of Japan

[73] Assignee: Sumitomo Electric Industries, Ltd., Osaka, Japan

[21] Appl. No.: 264,276

[22] Filed: Jun. 23, 1994

[30] Foreign Application Priority Data

Jun. 25, 1993 [JP] Japan .................................. 5-179798
Mar. 9, 1994 [JP] Japan .................................. 6-065672

[51] Int. Cl.$^6$ ...................................................... A61F 2/06
[52] U.S. Cl. ............................ 623/1; 623/2; 623/16; 606/228; 606/230; 606/231
[58] Field of Search .................................. 523/112, 113, 523/114, 115; 524/29; 623/1, 16, 2; 606/228, 230, 231

[56] References Cited

U.S. PATENT DOCUMENTS

| | | | |
|---|---|---|---|
| 3,688,317 | 9/1972 | Kurtz | 606/230 |
| 3,896,813 | 7/1975 | Kartz | 606/230 |
| 4,248,924 | 2/1981 | Okita . | |
| 4,277,429 | 7/1981 | Okita . | |
| 4,304,010 | 12/1981 | Mano | 606/230 |
| 4,306,318 | 12/1981 | Mano et al. | 623/1 |
| 4,321,711 | 3/1982 | Mano | 606/230 |
| 4,326,532 | 4/1982 | Hammar | 623/1 |
| 4,332,035 | 6/1982 | Mano . | |
| 4,612,337 | 9/1986 | Fox et al. | 523/113 |
| 4,713,070 | 12/1987 | Mano . | |
| 4,787,900 | 11/1988 | Yannas | 623/1 |
| 5,024,671 | 6/1991 | Tu et al. | 623/1 |
| 5,061,276 | 10/1991 | Tu et al. | 623/1 |
| 5,258,014 | 11/1993 | Harada et al. | 606/228 |

FOREIGN PATENT DOCUMENTS

| | | |
|---|---|---|
| 230635A3 | 12/1986 | European Pat. Off. . |
| 328421 | 2/1989 | European Pat. Off. . |
| 334046A2 | 2/1989 | European Pat. Off. . |
| 448840A2 | 12/1990 | European Pat. Off. . |
| 531547A1 | 3/1992 | European Pat. Off. . |
| 42-13560 | 8/1942 | Japan . |
| 55-76648 | 6/1980 | Japan . |
| 58-1656 | 1/1983 | Japan . |
| 60-3842 | 1/1985 | Japan . |
| 2-18977 | 4/1990 | Japan . |
| 91/15251 | 10/1991 | WIPO . |
| 92/09311 | 6/1992 | WIPO . |

OTHER PUBLICATIONS

"Control Of Prosthetic Bacterial Infection: Evaluation Of An Easily Incorporated, Tightly Bound, Silver Antibiotic PTFE Graft", Alan Benvenisty et al., Journal of Surgical research 44, 1–7 (1988).

"Prevention Of Vascular Prosthetic Infection With An Antibiotic–Bonded Dacron Graft", William Shue et al., Vascular Surgery, 8, pp. 600–605, 1988.

"Antibiotic Binding To Polytetrafluoroethylene Via Glucosaminoglycan–Keratin Luminal Coating", Kim Sobinsky et al, Surgery, 100, pp. 629–634 (1986).

"Use Of An Antibiotic–Bonded Graft For In Situ Reconstruction After Prosthetic Graft Infections", Michael Colburn et al., J. Vascular Surgery, 16, pp. 651–660 (1992).

*Primary Examiner*—Veronica P. Hoke
*Attorney, Agent, or Firm*—Lowe, Price, LeBlanc & Becker

[57] ABSTRACT

An antibacterial vascular prosthesis obtained by winding a tube, fiber or sheet formed from a polymeric material and combined with an antibacterial substance on the outer surface of a vascular prosthesis composed of a tubular porous body formed of a synthetic resin is provided. The antibacterial vascular prosthesis can exhibit an antibacterial activity over a long period of time without impairing the porous structure, antithrombogenicity and histocompatibility inherent in the vascular prosthesis composed of the tubular porous body formed of the synthetic resin. An antibacterial surgical suture comprising a tube or fiber formed from a polymeric material and combined with an antibacterial substance is also provided.

14 Claims, 1 Drawing Sheet

ANTIBACTERIAL VASCULAR PROSTHESIS AND SURGICAL SUTURE

FIELD OF THE INVENTION

The present invention relates to a vascular prosthesis suitable for use as a substitute for an artery, vein or the like and a surgical suture, and more particularly to a vascular prosthesis and a surgical suture, both, given with an antibacterial activity.

BACKGROUND OF THE INVENTION

Vascular prostheses composed of a tubular porous body formed of a synthetic resin such as polytetrafluoroethylene (hereinafter abbreviated as "PTFE") or polyester are widely used in repair of circulation or for internal shunts upon dialysis. However, such vascular prostheses involve a serious problem that they tend to be infected with bacteria. More specifically, the bacteria entered upon implantation of a vascular prosthesis, or the like are easy to proliferate on an artificial material such as the vascular prosthesis because an immune system, which is an innate protective system in the living body, is hard to normally and sufficiently operate in such circumstances. In addition, tissue cells and intracellular substances damaged or destroyed by grafting, or blood coagulation occurred in the damaged site provide suitable proliferative sites for the entered bacteria.

As methods for preventing the bacterial infection, for example, it has been conducted to sterilize a vascular prosthesis before its use, and to make a surgical field thoroughly sterile. However, the infection rate is considerably high as reported to be 1–5%. In order to treat an infectious disease, it is conducted to administer one or more antibiotics. By this method, however, it is difficult to topically exert their antibacterial effect on the site in which bacteria are grown. It has hence been only necessary to excise or remove the vascular prosthesis once it has become infected.

As methods for protecting a vascular prosthesis from bacterial infection, there have heretofore been proposed various methods in which an antibacterial activity is imparted to the vascular prosthesis itself. For example, there have been proposed (1) a vascular prosthesis obtained by applying or depositing a silver-antibiotic complex on a porous structure formed of PTFE or polyester [A. I. Benvenisty et al., J. Surgical Research, 44, 1–7 (1988)], and (2) a vascular prosthesis obtained by coating a PTFE or polyester material with a surfactant and then bonding an antibiotic to the surfactant by ionic bonding [W. B. Shue et al., J. Vascular Surgery, 8, 600–605 (1988)]. However, these methods have involved problems that it is impossible to last the antibacterial effect of the antibiotic over a long period of time until peripheral tissues including the interior of the wall of the vascular prosthesis become healed because the amount of the antibiotic combined is small, and that the antibiotic and surfactant present in the wall and on the inner wall surface of the vascular prosthesis impair the innate antithrombogenicity and histocompatibility in the vascular prosthesis.

In addition to the above methods, there have been proposed (3) methods in which a mixture of a biopolymer such as glucosaminoglycan-keratin or collagen and an antibiotic is applied onto the inner wall or outer surface of a vascular prosthesis [K. R. Sobinsky et al., Surgery, 100, 629–634 (1986), and M. D. Colburn et al., J. Vascular Surgery, 16, 651–660 (1992)]. According to these methods, the amount of the antibiotic to be combined can be increased, and the release rate of the antibiotic can be controlled. However, the methods have involved, in addition to a problem that the antibiotic and biopolymer present in the wall and on the inner wall surface of the vascular prosthesis impair the innate antithrombogenicity and histocompatibility in the vascular prosthesis, a problem that since the porous structure within the wall of the vascular prosthesis is filled with the biopolymer, the penetration of living tissues through the outer and inner walls is not caused to progress, and so the healing of the vascular prosthesis is not performed.

OBJECTS AND SUMMARY OF THE INVENTION

It is an object of the present invention to provide an antibacterial vascular prosthesis capable of exhibiting an antibacterial activity over a long period of time without impairing the porous structure, antithrombogenicity and histocompatibility inherent in a vascular prosthesis composed of a tubular porous body formed of a synthetic resin.

Another object of the present invention is to provide an antibacterial surgical suture.

The present inventors have carried out an extensive investigation with a view toward overcoming the above-described problems involved in the prior art. As a result, it has been found that the above object can be achieved by winding a tube, fiber or sheet composed of a polymeric material and combined with an antibacterial substance on the outer surface of a vascular prosthesis.

The tube, fiber or sheet combined with the antibacterial substance may be produced by impregnating with and/or depositing the antibacterial substance or a mixture of the antibacterial substance and a biodegradable polymer into and/or on the whole or parts of the pores, inner surface and outer surface of a porous tube, fiber or sheet formed from a polymeric material. The tube, fiber or sheet combined with the antibacterial substance may also be formed from a mixture of a biodegradable polymer and an antibacterial substance.

Since the tube, fiber or sheet combined with the antibacterial substance is wound on the outer surface of the vascular prosthesis with a desired space, the porous structure of the vascular prosthesis is not impaired, and besides the functions of the vascular prosthesis, such as antithrombogenicity and histocompatibility are not impeded. The antibacterial substance can be gradually released over a long period of time from the tube, fiber or sheet combined with the antibacterial substance. The antibacterial substance gradually released in the vicinity of the outer surface of the vascular prosthesis inhibits the growth of bacteria attached to the vascular prosthesis over a long period of time. Of these tube, fiber and sheet combined with the antibacterial substance, the tube or fiber may be used as an antibacterial surgical suture by itself.

The present invention has been led to completion on the basis of these findings.

According to the present invention, there is thus provided an antibacterial vascular prosthesis obtained by winding a tube, fiber or sheet formed from a polymeric material and combined with an antibacterial substance on the outer surface of a vascular prosthesis composed of a tubular porous body formed of a synthetic resin.

According to the present invention, there is also provided an antibacterial surgical suture comprising a tube or fiber formed from a polymeric material and combined with an antibacterial substance.

DETAILED DESCRIPTION OF THE INVENTION

Figure 1:
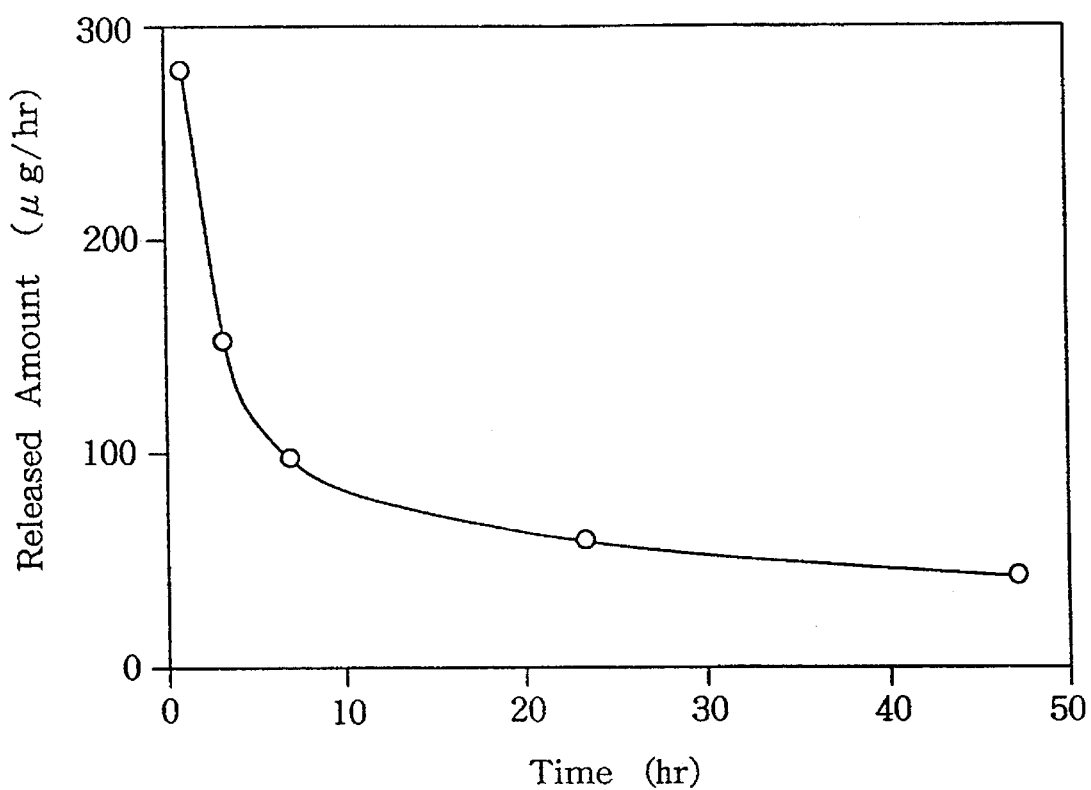
FIG. 1 diagrammatically illustrates the amount of an antibacterial substance released with time from an antibacterial vascular prosthesis obtained in an example of the present invention.

The present invention will hereinafter be described in detail.

Tubular porous body

In the present invention, a tubular porous body formed of a synthetic resin is used as a vascular prosthesis. Examples of the synthetic resin from which the vascular prosthesis is formed may include polytetrafluoroethylene, polyester, polyurethane, polyethylene, polypropylene, polysiloxane and the like.

No particular limitation is imposed on the process for producing the tubular porous bodies from these synthetic resin materials. They may be produced in accordance with a process known per se in the art according to the material used. For example, a tubular porous body made of PTFE can be produced in accordance with the process described in Japanese Patent Publication No. 13560/1967. More specifically, a liquid lubricant is first mixed into unsintered PTFE powder, and the mixture is extruded through a ram extruder into a tubular form. The tube is stretched at least in its axial direction after removing liquid lubricant from the tube or without removing the liquid lubricant. Both ends of the tube are then fixed so as to prevent it from shrinking, and the tube is heated from both inner and outer sides thereof at 327° C. which is a sintering temperature of PTFE, or higher, thereby obtaining a tubular PTFE porous body having a fine fibrous structure composed of fibers and knots joined to each other by the fibers.

When a continuous temperature gradient is given between the inner and outer surfaces of the PTFE tube upon the sintering in such a manner that the temperature of the outer surface is higher than that of the inner surface by 50°–300° C., the fiber-knot structure is rearranged from the inner surface of the tube to the outer surface, so that portions whose fibers are more stretched than those before the treatment and hence made longer, and portions whose fiber are made shorter than those before the treatment are obtained.

Besides, when portions of the PTFE tube after the stretching are heated further at a temperature of 327° C. or higher in accordance with the process described in Japanese patent Publication No. 1656/1983 or Japanese Patent Application Laid-Open No. 76648/1980, a tubular PTFE porous body excellent in strength in the direction perpendicular to the stretching direction can be produced.

Tube, fiber and sheet combined with antibacterial substance

The tube, fiber or sheet combined with the antibacterial substance can be produced by (1) a process in which an antibacterial substance is mixed and dispersed in a polymeric material, and the resulting mixture is formed into a tube, fiber or sheet, (2) a process in which an antibacterial substance is impregnated into and/or deposited on a porous tube, fiber or sheet formed from a polymeric material, (3) a process in which a mixture of a biodegradable polymer and an antibacterial substance is impregnated into and/or deposited on a porous tube, fiber or sheet formed from a polymeric material, or the like.

In the process in which the mixture of the polymeric material and the antibacterial substance is formed into the tube, fiber or sheet, the tube, fiber or sheet may preferably be made porous.

In the process in which the antibacterial substance or the mixture of the biodegradable polymer and the antibacterial substance is impregnated into and/or deposited on the porous tube, fiber or sheet formed from the polymeric material, the antibacterial substance or the mixture of the biodegradable polymer and the antibacterial substance is impregnated into and/or deposited on the inner and outer surfaces of the porous tube, the outer surface of the porous fiber, the outer surface of the porous sheet and the inner surfaces defining pores in these porous bodies. The impregnation and/or deposition may be performed to the whole or parts of the pores, inner surface and outer surface of the porous tube, fiber or sheet. The antibacterial substance or the mixture of the biodegradable polymer and the antibacterial substance may be only impregnated into the pores in the porous body and deposited on the inner surfaces defining the pores in the porous body. In this invention, the term "impregnation" means that the antibacterial substance or the mixture of the biodegradable polymer and the antibacterial substance is impregnated into void spaces (i.e., pores) in the porous body to hold it therein. On the other hand, the term "deposition" means that the antibacterial substance or the mixture of the biodegradable polymer and the antibacterial substance is deposited on the inner surface (in the case of the porous tube) and outer surface of the porous body and the inner surfaces defining the pores in the porous body. In fact, both impregnation and deposition often take place.

Examples of the polymeric material from which the porous tube, fiber or sheet is formed may include synthetic polymeric materials such as polytetrafluoroethylene, tetrafluoroethylene-hexafluoropropylene copolymers, polyester, polyurethane, polyethylene and polypropylene. Besides, as the polymeric material, may be used biodegradable polymers (biotransformable polymers) such as agarose, dextran, polylactic acid, gelatin, fibrinogen, chitin and chitosan.

No particular limitation is imposed on the process for producing the porous tubes, fibers or sheets from these synthetic resin materials. For example, in the case where PTFE is used as a polymeric material, a porous tube may be produced in the same manner as in the tubular PTFE porous body in the vascular prosthesis described above. Following the process described in Japanese Patent Publication No. 18977/1990, PTFE containing a liquid lubricant may be formed into a fine rod. After removing the liquid lubricant, the rod may be stretched in its longitudinal direction into a porous fiber. Alternatively, a porous sheet may be produced in accordance with the process described in Japanese Patent Publication No. 3842/1985. Similarly, a porous tube may be formed by producing a porous thin-film material composed of PTFE in advance, winding the thin-film material on a metallic wire to fix it and then integrally sintering the thin-film material under heat.

No particular limitation is also imposed on the process for producing the porous tubes, fibers or sheets from the biodegradable polymers. Examples thereof may include (1) a process for producing a tube composed of a biodegradable polymer, in which a solution of the biodegradable polymer is coated on the outer wall surface of a tube made of a suitable material to dry the polymer, and the tube situated inside the biodegradable polymer is then drawn out in this state, (2) a process for forming a fiber, in which a solution of a biodegradable polymer is filled into the bore of a tube made of a suitable material to dry the polymer, and the dried polymer is then drawn out of the tube, and (3) a process in which a solution of a biodegradable polymer is spread on a flat plate made of a suitable material, and the polymer is then dried.

In the process for producing the tube, fiber or sheet from the mixture of the polymeric material and the antibacterial substance, it is preferable that the biodegradable polymer be used as the polymeric material. In this case, when a mixed solution obtained by mixing a solution of the biodegradable polymer and the antibacterial substance in advance is used in the above-described production process of the tube, fiber or sheet composed of the biodegradable polymer, the antibacterial substance can be evenly dispersed in the biodegradable polymer, whereby the antibacterial substance can be dispersed and fixed in the biodegradable polymer in the form of a tube, fiber or sheet after drying the polymer. The antibacterial substance may bond to the biodegradable polymer by ionic bonding. As a solvent, there is generally used an organic solvent which does not decompose the biodegradable polymer and antibacterial substance. The tube, fiber or sheet composed of the biodegradable polymer is preferably made porous. The tube, fiber or sheet composed of the biodegradable polymer and combined with the antibacterial substance in accordance with this process can gradually release the antibacterial substance over a long period of time.

In the method of impregnating with and/or depositing the antibacterial substance into and/or on the porous tube, fiber or sheet formed from the polymeric material, it is only necessary to immerse the porous tube, fiber or sheet in a solution with the antibacterial substance dissolved therein and then dry the porous body. By this method, the antibacterial substance can be impregnated into and/or deposited on the whole or part of the pores, inner surface and outer surface of the porous body.

In order to control the release of the antibacterial substance over a long period of time, it is preferable that a mixture of the biodegradable polymer and the antibacterial substance be impregnated into and/or deposited on the porous tube, fiber or sheet formed from the polymeric material. In this method, it is only necessary to immerse the porous tube, fiber or sheet in a mixed solution of the biodegradable polymer and the antibacterial substance and then dry the porous body. By this method, the antibacterial substance evenly dispersed in the biodegradable polymer can be impregnated into and/or deposited on the whole or part of the pores, inner surface and outer surface of the porous body. In this case, the above-mentioned various biodegradable polymers may be used as the biodegradable polymer. As a solvent, there is generally used a volatile organic solvent which can enter void spaces in the porous body and does not decompose the biodegradable polymer and antibacterial substance.

As the antibacterial substance, may be used antibiotics such as β-lactam, aminoglycoside, chloramphenicol, tetracycline, macrolide and lincomycin and heavy metals such as silver compounds. These substances may be used either singly or in any combination thereof.

The tube, fiber or sheet combined with the antibacterial substance is wound on the outer surface of the vascular prosthesis. However, it is wound with a desired space, not on the whole outer surface, so that the porous structure of the vascular prosthesis is not impaired. It is desirable that the outer diameter (size) of the tube or fiber combined with the antibacterial substance, or the thickness and width of the sheet combined with the antibacterial substance be smaller than the outer diameter of the vascular prosthesis, for example, about a half or smaller, preferably about a third or smaller, more preferably about a fourth or smaller of the outer diameter of the vascular prosthesis.

The release rate of the antibacterial substance is basically determined by the diffusion rate in the humor in which the antibacterial substance exudes after the implantation of the antibacterial vascular prosthesis according to the present invention. However, it may be controlled by selecting the pore size, porosity, wall thickness, size or width of the porous tube, fiber or sheet combined with the antibacterial substance, the kind of the biodegradable polymer, the compositional ratio of the biodegradable polymer to the antibacterial substance, the bonding between the biodegradable polymer and the antibacterial substance, the winding pitch on the vascular prosthesis of the tube, fiber or sheet, or the like. The combined amount of the antibacterial substance can be suitably determined. According to the present invention, however, it is possible to combine the antibacterial substance in a comparatively great amount compared with the conventional methods in which the antibacterial substance is bonded to the vascular prosthesis itself because the antibacterial substance is combined with the tube, fiber or sheet composed of the polymeric material. It is therefore possible to combine the antibacterial substance in an amount sufficient to gradually release it until an immune system normally operates in vivo after the implantation of the vascular prosthesis. The amount can be experimentally determined from the kind and release rate of the antibacterial substance, and the like by those skilled in the art.

Since the antibacterial substance and the tube, fiber or sheet combined with the antibacterial substance exist only on the outer surface of the vascular prosthesis, they do not directly contact with the blood stream. Therefore, the innate antithrombogenicity in the vascular prosthesis is not impaired. According to the antibacterial vascular prosthesis of the present invention, the antibacterial substance released exists only on the outer surface of the vascular prosthesis or in its wall in the vicinity of the outer surface. Therefore, the histocompatibility of the vascular prosthesis is not impaired. Besides, since the porous structure of the vascular prosthesis is maintained, the penetrability of living tissues through the vascular prosthesis is kept good, and so the healing process is also not inhibited.

After the implantation of the antibacterial vascular prosthesis according to the present invention, the antibacterial substance is released near the outer surface of the vascular prosthesis. In this case, the antibacterial substance is gradually released over a long period of time owing to such that a sufficient amount of the antibacterial substance can be combined with the tube, fiber or sheet, and that such a combination of the antibacterial substance permits the control of release rate. The gradual release of the antibacterial substance allows the antibacterial substance to inhibit the growth of bacteria attached to the outer surface of the main vascular prosthesis over a long period of time. Meanwhile, the innate immune system in the living body comes to fully operate, and the tissues penetrates into the main vascular prosthesis, so that the healing is caused to progress.

The tube or fiber according to the present invention, which has been formed from the polymeric material and combined with the antibacterial substance, is also useful in applying to a surgical suture by itself. An incision site upon surgery has the highest possibility of being the source of infection. However, the use of the surgical suture composed of the tube or fiber combined with the antibacterial substance in such a site permits inhibiting the growth of the bacteria attached to the incision site as the source of infection over a long period of time because the antibacterial substance is gradually released over a long period of time.

ADVANTAGES OF THE INVENTION

According to the present invention, there is provided an antibacterial vascular prosthesis capable of exhibiting an antibacterial activity over a long period of time without impairing the porous structure, antithrombogenicity and histocompatibility inherent in a vascular prosthesis composed of a tubular porous body formed of a synthetic resin.

The present invention also provides an antibacterial surgical suture capable of exhibiting an antibacterial activity over a long period of time.

EMBODIMENTS OF THE INVENTION

The present invention will hereinafter be described more specifically by the following examples. However, it should be borne in mind that this invention is not limited to and by these examples only.

EXAMPLE 1

One gram of ofloxacin (antibiotic, product of Daiich Seiyaku Co., Ltd.) was suspended in 10 ml of a 1% solution of polylactic acid (molecular weight: 50,000, product of Polyscience Co.) in dioxane (product of Wako Pure Chemical Industries, Ltd.) which had been prepared in advance.

After a tape obtained by cutting a porous PTFE sheet (LUP-300, product of Sumitomo Electric Industries, Ltd.) into a width of 5 mm was spirally wound at the pitch of 2.5 mm on a stainless steel rod 1 mm in outer diameter, both ends of the tape were fixed to the rod, followed by heating of the tape at a temperature not lower than the melting point of PTFE to integrally sinter the tape, thereby forming the tape in the form of a tube. The stainless steel rod was then drawn out of the tube.

The porous PTFE tube thus obtained was immersed in the above-prepared mixed solution of ofloxacin and polylactic acid in dioxane to sufficiently penetrate the solution into the wall of the porous body. The thus-treated tube was then air-dried. This procedure was repeated 3 times, whereby the mixture of polylactic acid and ofloxacin was impregnated into the wall and deposited on the inner surface of the tube to obtain a composite tube.

The thus-obtained tube combined with ofloxacin and polylactic acid was lightly immersed in a 1% solution of polylactic acid in dioxane to wash out polylactic acid and ofloxacin present on the outer surface of the tube and at the same time, soften the tube as a whole. Thereafter, the tube was wound at a pitch of 5 mm on a stretched PTFE vascular prosthesis (Technograft, product of Sumitomo Electric Industries, Ltd.) 4 mm across and 5 cm long and then air-dried.

Both ends of the thus-obtained antibacterial vascular prosthesis were separately connected to a silicone tube, and a PBS solution (phosphate buffered-saline solution) was caused to flow at a rate of 10 ml/min through the bore of the tube by a peristaltic pump. At the same time, only the part of the vascular prosthesis was immersed in the same PBS solution as described above in a beaker to determine whether ofloxacin was dissolved out of the inner surface and outer surface of the vascular prosthesis by the measurement of absorbance at 280 nm of the PBS solution. As a result, no dissolving-out of ofloxacin from the inner surface of the vascular prosthesis was detected. As illustrated in FIG. 1, however, ofloxacin was gradually being released from the outer surface of the vascular prosthesis even after 48 hours.

The antibacterial activity against *Escherichia coli* (JM109) of the antibacterial vascular prosthesis obtained above was evaluated. On an agar LB medium (1% bactotryptone, 0.5% yeast extract, 0.5% common salt, 1.5% agar) on a plate 10 cm across, were spread $10^4$ cells of *Escherichia coli*. The antibacterial vascular prosthesis 1 cm long was left at rest in the center of the medium, and the cells were then cultured at 37° C. for 18 hours. As a result, no proliferation of *Escherichia coli* was observed within a radius of 22 mm from the antibacterial vascular prosthesis. It was hence confirmed that the antibacterial vascular prosthesis according to the present invention has excellent antibacterial activity.

EXAMPLE 2

A tube combined with ofloxacin and polylactic acid, which had been produced in the same manner as in Example 1, was wound 75 mm in length on a stretched PTFE vascular prosthesis (Technograft) 4 mm across and 5 cm long. The thus-obtained composite vascular prosthesis was implanted under the back skin of a rabbit (New Zealand White, male). After a week, the back was incised to take the prosthesis sample out of the back. The sample was evaluated in the antibacterial activity against *Escherichia coli* (JM109) in the same manner as in Example 1. As a result, no proliferation of *Escherichia coli* was observed within a radius of 17 mm from the sample. It was hence confirmed that the antibacterial vascular prosthesis according to the present invention has excellent antibacterial activity even in the living body.

We claim:

1. An antibacterial vascular prosthesis obtained by winding a tube, fiber or sheet formed from a polymeric material and combined with an antibacterial substance on the outer surface of a vascular prosthesis composed of a tubular porous body formed of a synthetic resin, wherein the tube, fiber or sheet combined with an antibacterial substance is wound on the outer surface of the vascular prosthesis such that portions of the outer surface of the antibacterial vascular prosthesis are uncovered and the porosity of the antibacterial vascular prosthesis is substantially unimpaired.

2. The antibacterial vascular prosthesis according to claim 1, wherein the tube, fiber or sheet combined with the antibacterial substance is obtained by impregnating with and/or depositing the antibacterial substance into and/or on at least part of the pores, inner surface and outer surface of a porous tube, fiber or sheet formed from the polymeric material.

3. The antibacterial vascular prosthesis according to claim 2, wherein the polymeric material from which the porous tube, fiber or sheet is formed is polytetrafluoroethylene or a tetrafluoroethylene-hexafluoropropylene copolymer.

4. The antibacterial vascular prosthesis according to claim 1, wherein the tube, fiber or sheet combined with the antibacterial substance is obtained by impregnating with and/or depositing a mixture of a biodegradable polymer and the antibacterial substance into and/or on at least part of the pores, inner surface and outer surface of a porous tube, fiber or sheet formed from the polymeric material.

5. The antibacterial vascular prosthesis according to claim 4, wherein the polymeric material from which the porous tube, fiber or sheet is formed is polytetrafluoroethylene or a tetrafluoroethylene-hexafluoropropylene copolymer.

6. The antibacterial vascular prosthesis according to claim 4, wherein the biodegradable polymer is selected from agarose, dextran, polylactic acid, gelatin, fibrinogen, chitin and chitosan.

7. The antibacterial vascular prosthesis according to claim 1, wherein the tube, fiber or sheet combined with an antibacterial substance is formed from a mixture of a biodegradable polymer and the antibacterial substance.

8. The antibacterial vascular prosthesis according to claim 7, wherein the biodegradable polymer is selected from agarose, dextran, polylactic acid, gelatin, fibrinogen, chitin and chitosan.

9. The antibacterial vascular prosthesis according to claim 1, wherein the antibacterial substance is an antibiotic or a heavy metal.

10. The antibacterial vascular prosthesis according to claim 9, wherein the antibiotic is selected from β-lactam, aminoglycoside, chloramphenicol, tetracycline, macrolide and lincomycin.

11. The antibacterial vascular prosthesis according to claim 9, wherein the heavy metal is a silver compound.

12. The antibacterial vascular prosthesis according to claim 1, wherein the outer diameter of the tube combined with the antibacterial substance, the size of the fiber combined with the antibacterial substance, or the thickness and width of the sheet combined with the antibacterial substance are smaller than the outer diameter of the vascular prosthesis.

13. The antibacterial vascular prosthesis according to claim 1, wherein the outer diameter of the tube combined with the antibacterial substance, the size of the fiber combined with the antibacterial substance, or the thickness and width of the sheet combined with the antibacterial substance are about a half or smaller of the outer diameter of the vascular prosthesis.

14. The antibacterial vascular prosthesis according to claim 1, wherein the tubular porous body composing the vascular prosthesis and made of a synthetic resin is a tubular porous body formed from polytetrafluoroethylene.

* * * * *